United States Patent [19]

Nash-Morgan

[11] Patent Number: 5,116,675
[45] Date of Patent: May 26, 1992

[54] DISPOSABLE, ELASTICIZED ADHESIVE NECK AND FACIAL WRINKLE GATHERING DEVICE

[76] Inventor: Leonora E. Nash-Morgan, 3524 E. Forest Lake Dr., Sarasota, Fla. 34232

[21] Appl. No.: 751,156

[22] Filed: Aug. 28, 1991

[51] Int. Cl.⁵ .............................. A61F 13/12
[52] U.S. Cl. ................... 428/343; 428/230; 428/231; 428/232; 602/74
[58] Field of Search ............ 128/164, 163; 428/343, 428/230, 232, 231, 294

[56] References Cited

U.S. PATENT DOCUMENTS

| | | | |
|---|---|---|---|
| 1,023,358 | 4/1912 | Bender | 128/164 |
| 1,996,703 | 4/1935 | Giuliano | 128/164 |
| 3,709,225 | 1/1973 | Sobel | 128/164 X |
| 4,366,814 | 1/1983 | Riedel | 428/230 X |
| 4,658,811 | 4/1987 | Beaird | 128/163 |
| 4,734,320 | 3/1988 | Ohira et al. | 428/231 |
| 4,907,580 | 3/1990 | Leonardi | 128/163 |
| 4,934,357 | 6/1990 | Frantzich et al. | 128/164 |

Primary Examiner—George F. Lesmes
Assistant Examiner—D. R. Zirker
Attorney, Agent, or Firm—Charles J. Prescott

[57] ABSTRACT

A disposable adhesive neck and facial wrinkle gathering device which includes a central elastic portion and opposingly extending non-elastic adhesive strips each connected at one end to the elastic portion. The central elastic portion is formed of a thin sheet of flexible, elastically extendable or stretchable material, preferably so in all directions. The adhesive strips may be either transparent, translucent or skin-colored and are sized in length to extend either partially around to the sides of the user's neck from the nape of the neck or downwardly from around the top of the base of the ear along either side of the ear. When so positioned, with the central elastic portion stretched, the adhesive strips draw facial and neck skin toward the central elastic portion to stretch and flatten wrinkles and flabby tissue.

7 Claims, 2 Drawing Sheets

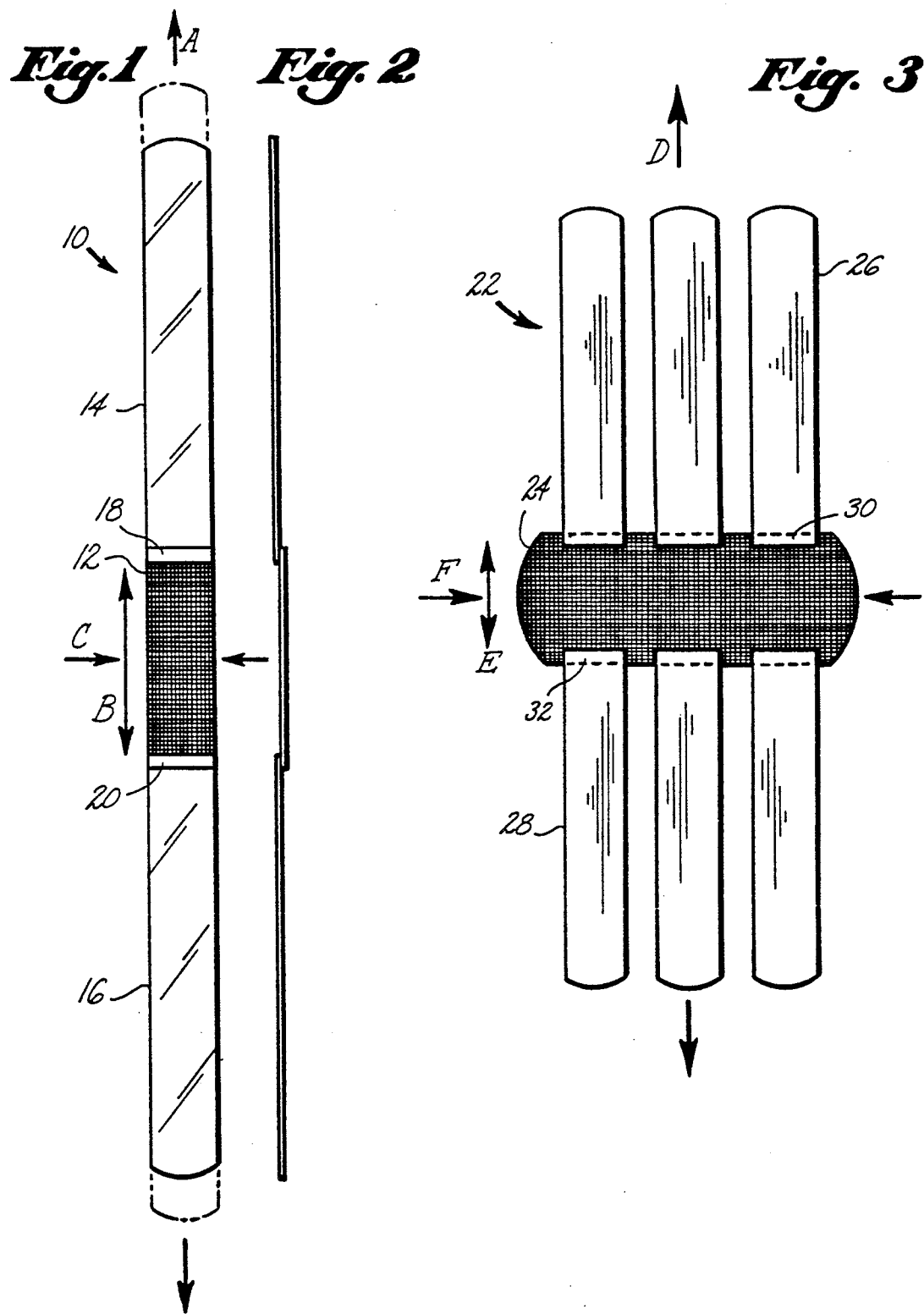

5,116,675

DISPOSABLE, ELASTICIZED ADHESIVE NECK AND FACIAL WRINKLE GATHERING DEVICE

BACKGROUND OF THE INVENTION

This invention generally relates to elasticized adhesive strips, and more particularly to a disposable elasticized adhesive neck and facial wrinkle gathering device.

As men and women age, the neck and facial muscles and skin tissue generally lose muscle tone and become wrinkled and flaccid. The appearance of wrinkles in the lower face, neck and under jaw area are some of the more prominent facial features which exhibit this aging characteristic.

To alleviate this problem for those unable to deal with this aging process, cosmetic surgery or "face lift" to remove excess skin tissue has provided one alternative to maintaining a more youthful appearance.

Some chemical cosmetic products are also available which may tend to moisten and/or cause the skin to temporary contract or shrink so as to reduce the unsightliness of facial, chin and neck wrinkles. Additionally, heavier applications of conventional make-up also serve to disguise these aging effects.

The present invention provides a conveniently usable, disposable and economical alternative to the above presently available techniques for retarding the appearance of aging. This invention thus provides an elasticized adhesive neck and facial wrinkle gathering device which is intended to be worn for relatively short periods of time and which will stretch and draw wrinkled skin away from the more visible areas of the neck and lower jaw and face rearwardly and upwardly, respectively so as to smooth the broader areas of wrinkled skin in these areas. Although not a permanent or long lasting remedy for facial wrinkles, nonetheless, the present invention allows the user to apply this invention prior to public appearances and to enjoy the psychological benefits of a "face lift" during those brief time periods.

BRIEF SUMMARY OF THE INVENTION

This invention is directed to a disposable adhesive neck and facial wrinkle gathering device which includes a central elastic portion and oppositely extending non-elastic adhesive strips each connected at one end to the elastic portion. The central elastic portion is formed of a thin sheet of flexible, elastically extendable or stretchable material, praferably so in all directions. The adhesive strips may be either transparent, translucent or skin-colored and are sized in length to extend either partially around to the sides of the user's neck from the nape of the neck or downwardly from around the top of the base of the ear along either side of the ear. When so positioned, with the central elastic portion stretched, the adhesive strips draw facial and neck skin toward the central elastic portion to stretch and flatten wrinkles.

It is therefore an object of this invention to provide a disposable elasticized adhesive neck and facial wrinkle gathering device which is easily applied by the user for the temporary smoothing and stretching of prominent wrinkled skin of the lower face and neck and jaw area.

It is another object of this invention to provide a disposable elasticized neck and facial wrinkle gathering device which is an economical and easily user-implemented alternative to "face lifts" for achieving a temporary more youthful facial appearance.

It is another object of this invention to provide a disposable and unobtrusive means for temporarily stretching wrinkled skin in more prominent areas of the face and neck and gathering it in less prominent areas.

In accordance with these and other objects which will become apparent hereinafter, the instant invention will now be described with reference to the accompanying drawings.

BRIEF DESCRIPTION OF THE DRAWINGS

FIG. 1 is a front elevation view of one embodiment of the invention.

FIG. 2 is a side elevation view of FIG. 1.

FIG. 3 is a front elevation view of an alternate embodiment of the invention.

DETAILED DESCRIPTION OF THE INVENTION

Figure 4:
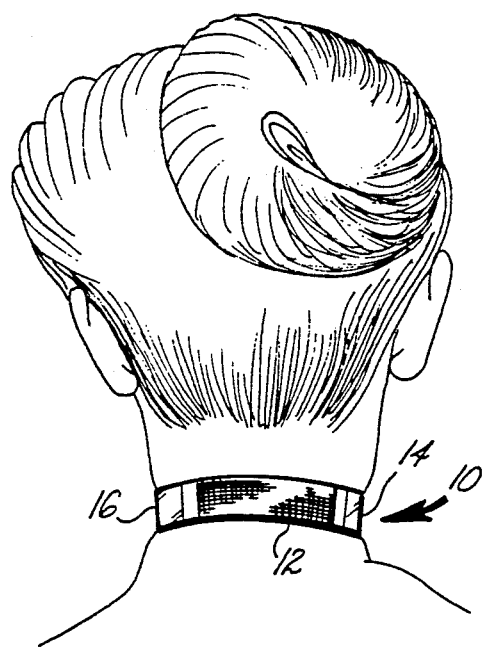
FIG. 4 is a rear perspective view of the invention shown in FIG. 1 in use attached around the nape and sides of a user's neck.

Referring now to the drawings, and particularly to FIGS. 1 and 2, the preferred embodiment of the invention is shown generally at numeral 10. This device 10 includes a central elongated rectangular sheet of thin elastic material 12 which is connected along opposing margins at 18 and 20 to very thin elongated strips of non-elastic adhesive material 14 and 16. These adhesive strips 14 and 16 are adhesive only on one surface thereof having releasable skin-adhering characteristics. Bonding between the central elastic sheet 12 and the non-elastic adhesive strips 14 and 16 in areas 18 and 20 is by conventional means such as heat sealing, stitching or adhesives.

The preferred embodiment of the elastic sheet 12 is a material which stretches in all directions such as available under the trademark SPANDEX. Other well-known "omni-elastic" polyester materials may be utilized for this purpose. The primary requirement is that the material be highly elastic and stretchable so that, when adhesive strips 14 and 16 are pulled in the direction of arrow A, elastic sheet 12 is elongated significantly (10-15% of its static length) in the direction of arrow B, somewhat narrowing in the direction of arrow C. Conventional adhesive cover sheets (not shown) may be provided so as to conceal the adhesive surfaces of adhesive strips 14 and 16 prior to use. Note that the entire device 10 preferably has a uniform width.

Referring now to FIG. 3, an alternate embodiment of the invention is shown generally at numeral 22 and includes a laterally extending generally rectangular central elastic sheet 24 having a plurality of non-elastic adhesive strips 26 and 28 extending in opposite directions from the margins of elastic sheet 24 as shown. This arrangement is provided so as to give a broader application and effectiveness of the invention as will be described herebelow with respect to FIGS. 4 and 5. The central elastic sheet 24 will elongate significantly in the direction of arrow E when adhesive strips 26 and 28 are manually pulled in the direction of arrows D, elastic sheet 24 also being reduced dimensionally in the direction of arrow B at the same time as a consequence of its stretching in the direction of arrow E. Adhesive strips 26 and 28 are again attached at 30 and 32 to elastic sheet 24 by conventional mechanical, chemical or heat bonding means.

Figure 5:
FIG. 5 is a front perspective view of FIG. 4.

Referring now to FIGS. 4 and 5, the preferred embodiment 10 is shown there in use. The central elastic sheet 12 has been stretched or elongated manually to near or at its maximum level of extensibility by pulling the non-elastic adhesive strips 14 and 16 oppositely in the direction of arrow A in FIG. 1. Thereafter, the adhesive surfaces of 14 and 16 are applied against the sides of the neck and adhered in place by manual pressure. By this arrangement, the tension exerted by the stretched elastic sheet 12 draws the skin in the front and sides of the neck rearwardly in the direction of arrows G and H in FIG. 5. This has the effect of flattening and smoothing the wrinkled areas in this facial and neck region. Due to the thin, light-weight nature of the device, it may be worn in place for several hours without discomfort.

With respect to the embodiment 22 in FIG. 3, a similar installation as depicted in FIG. 4 and FIG. 5 may be utilized. However, the embodiment 22, having a plurality of adhesive strips 26 and 28, will have a broader effect upon wrinkle removal in the neck and lower chin area.

Figure 6:
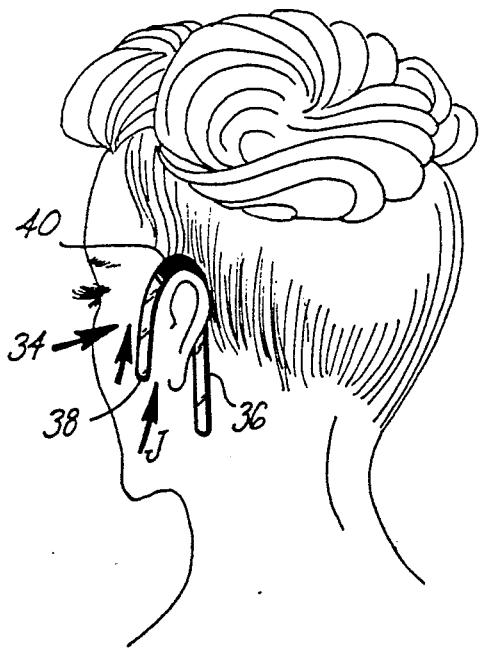
FIG. 6 is a rear perspective view of yet another embodiment of the invention in use.
Figure 7:
FIG. 7 is a front perspective view of FIG. 6.

Referring now to FIGS. 6 and 7, yet another embodiment of the invention is shown generally at numeral 34 which is structured similar to FIG. 1. However, this embodiment 34 is formed considerably more narrowly so that elastic sheet 40 will comfortably fit around the top of the base of the ear and elastic strips 36 and 38 will adhere along side the front and rear of the ear as shown. When stretched prior to the adhesive connection, elastic sheet 40 will thus draw the skin in the jaw and upper neck upward in the direction of arrow J. Again, this skin movement will result in the diminishing of the appearance of skin wrinkles and will also temporarily increase the firmness of the skin in these facial areas while in use.

It is emphasized that the present invention is intended to be a disposable and temporarily used device and is not intended to be left adhered in place for long periods of time. There are no benefits, claimed or anticipated after removal of the invention. Various transparent, translucent and skin-colored materials may be used for both the adhesive strips and the elastic central portions. The embodiment 10 in FIGS. 1 and 2 is shown having transparent adhesive strips 14 and 16, while the embodiment 22 shown in FIG. 3 depicts opaque, skin-colored adhesive strips 26 and 28.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A disposable neck and facial wrinkle gathering device structured for unobtrusive appearance when worn cosmetically for short periods of time comprising:
    a central elastic portion formed of a thin sheet of flexible elastic material;
    elongated non-elastic strips having an adhesive surface and connected at one end along each of two opposing end margins of said central portion and oppositely extending in either direction therefrom;
    said adhesive strips sized in length to partially encircle a user's neck about halfway therearound and to adhere in opposing position to either side of the neck when said elastic portion is stretched and positioned centrally against the nape of the neck in the region just below the user's hairline;
    said stretched elastic portion elastically acting through and supported only by said adhesive strips adhered to the sides of the neck to draw skin on the anterior of the neck rearwardly whereby wrinkles in the neck anterior skin are stretched and generally flattened;
    said elastic portion formed of spandex material which is elastic and stretchable in all directions within a plane defined by said elastic portion when flat.

2. A disposable elasticized adhesive neck and facial wrinkle gathering device as set forth in claim 1, wherein:
    said adhesive strips are translucent.

3. A disposable elasticized adhesive neck and facial wrinkle gathering device as set forth in claim 1, wherein:
    said adhesive strips are flesh-colored.

4. A disposable neck and facial wrinkle gathering device structured for unobtrusive appearance when worn cosmetically for short periods of time comprising:
    a central elastic portion formed of a thin sheet of flexible, elastic material;
    a plurality of elongated non-elastic strips each having an adhesive surface and each connected at one end along each of two opposing margins of said central portion and generally oppositely extending in either direction from each said margin;
    each adhesive strip of said plurality of adhesive strips sized in length to partially encircle a user's neck and to adhere in opposing position to either side of the neck when said elastic portion is stretched and positioned centrally against the nape of the neck in the region just below the user's hairline;
    said stretched elastic portion elastically acting through and supported only by said adhesive strips adhered to the sides of the neck to draw skin on the anterior of the neck rearwardly whereby wrinkles in the neck anterior skin are stretched and generally flattened.

5. A disposable elasticized adhesive neck and facial wrinkle gathering device as set forth in claim 5, wherein:
    said adhesive strips are translucent.

6. A disposable elasticized adhesive neck and facial wrinkle gathering device as set forth in claim 5, wherein:
    said adhesive strips are flesh-colored.

7. A disposable elasticized adhesive neck and facial wrinkle gathering device as set forth in claim 5, wherein:
    said elastic portion is formed of spandex material which is elastic and stretchable in all directions within a plane defined by said elastic portion when flat.

* * * * *